United States Patent [19]

Martin

[11] Patent Number: 5,648,403

[45] Date of Patent: Jul. 15, 1997

[54] ANTIMICROBIAL GUTTA PERCHA CONE

[76] Inventor: Howard Martin, 1106 Spring St., Silver Spring, Md. 20910

[21] Appl. No.: 543,377

[22] Filed: Oct. 16, 1995

[51] Int. Cl.$^6$ ............................................. A61K 6/08
[52] U.S. Cl. ..................... 523/117; 523/105; 523/115; 523/116; 524/763; 524/462; 524/436; 524/432; 433/228.1
[58] Field of Search ............................. 523/115, 116, 523/117, 105; 524/763, 462, 436, 432; 433/228.1

[56] References Cited

U.S. PATENT DOCUMENTS 4,931,096  6/1990  Fujisawa et al. .................... 523/115
5,234,971  8/1993  Imai et al. ........................... 523/113

FOREIGN PATENT DOCUMENTS 0050457  4/1982  European Pat. Off. ............. 523/113

*Primary Examiner*—Andrew E. C. Merriam
*Attorney, Agent, or Firm*—Walter G. Finch

[57] ABSTRACT

The present invention provides for a new formulation for antimicrobial gutta percha cones for obturation of root canals comprising of 20% gutta percha, 55% zinc oxide, 10% Barium, 10% sulphate, 10% triiodomethane, and 5% wax/resin. In order to ensure pliability and compactability, this formula should be varied by no more than 10%.

1 Claim, No Drawings

ANTIMICROBIAL GUTTA PERCHA CONE

BACKGROUND OF THE INVENTION

This application relates to root canals. More particularly, this application relates to an improvement on the current material used for root canal obturation, the shaped gutta percha cone.

The purpose for filling the root canal is to seal in any remaining microorganisms so they do not come into contact with tissue, and to eliminate the possibility of bacterial attraction to the inflamed area. Complete obturation of the root canal is necessary to prohibit periapical exudate from draining into the canal, thereby either becoming an irritant itself or attracting bacterial contamination known as anachoresis.

The current method of obturating the root canal is by inserting a shaped cone of gutta percha, the material of choice since its introduction in 1867, into the prepared root canal. The basic formulation of gutta percha cones has not changed in over fifty years, except in the new milling process which changes the alpha form of gutta percha to the more easily moldable beta form. The general composition of the cone is: 20% gutta percha, a coagulated latex which is a trans isomer of rubber to serve as the matrix; 66% zinc oxide, as filler material; 10% barium or strontium, as the radiopacifier; 3% waxes or resins; 0.3% color pigments; small amounts of antioxidants and plasticizers. The above formula may vary slightly by manufacturer.

Gutta percha has been shown to be inert by numerous studies and is desirable because it does not shrink, is relatively non-irritating to tissue, non-staining, radiopaque, and can be molded to improve its adaptability. The newer version of this material is a highly milled form which allows improved physical adaptability.

Unfortunately, the newer beta form is more difficult to control and insert into the canal, and cannot easily be removed for retreatment of the root canal since it contains a metal core. Even the original alpha form of gutta percha is not always easily inserted into the root canal due to size restrictions or the curvatures of the canal. Although the current gutta percha cones are pliable, they do not fully conform to the anatomy of the root canal. Therefore, due to irregularities in the shapes of the canals, the gutta percha cones cannot always completely seal off the canal. They may not obturate the canal apically and they may not do so laterally. And if the canals are ovoid at the apex, the cones may not fully seal the apical foramen of the canal.

With the root canal only partially sealed, the chance of having difficulties with irritation of the affected area or bacterial contamination increases leading to infection and failure of the root canal. Even when the cone does seal the opening of the canal completely or almost completely, a gradual leaching out process from contact with tissue fluid will create more voids and poorer adaptation within the canal anatomy. The level of discomfort and pain associated with an irritated, inflamed, and/or infected root canal area can be great, followed by loss of the tooth. More importantly, with the present root canal filling material, these can be recurring problems leading to tooth extraction.

For the foregoing reasons, there is a need for a root canal filling material which is more pliable and gives additional protection against irritation and infection which current gutta percha cones do not provide. The antimicrobial gutta percha cone can fulfill this need.

SUMMARY OF THE INVENTION

A new formulation for antimicrobial gutta percha cones which satisfies this need comprises:

| | |
|---|---|
| gutta percha | 20% |
| zinc oxide | 55%–60% |
| barium sulphate | 10% |
| triiodomethane | 10% |
| wax/resin | 5% |

In order to ensure pliability and compactability, this formula should be varied by no more than 10%.

OBJECTS OF THE INVENTION

Therefore it is an object of the present invention to provide for gutta percha cones with decreased brittleness and tissue irritation.

It is another object of the present invention to provide for gutta percha cones which are more conformable to the anatomy of the root canal.

It is still another object of the present invention to provide for safeguards against irritation and infection in addition to sealing the root canal.

It is a further object of the present invention to decrease the potential of infection at the root canal area.

It is yet a further object of the present invention to provide an additional layer of protection against irritation and infection only once the seal created by the gutta percha cone begins to degrade.

DETAILED DESCRIPTION OF THE INVENTION

The present invention is directed to a formulation of the gutta percha cone which provides the necessary safeguards against irritation and infection due to incomplete obturation of the root canal, while at the same time be more conformable to the canal anatomy.

The high level of zinc oxide, the material used as filler for the gutta percha cones, causes the cones to be more brittle and prone to breakage upon insertion into the root canal. In addition, it has been shown that the leaching out of zinc oxide over time has lead to increased tissue irritation. The present invention is formulated with a reduced amount of zinc oxide to decrease brittleness of the cone and tissue irritation.

Iodine is known for its mild effect on living tissue and has bactericidal ability over a wide range of pH against a broad spectrum of pathogens. It is effective on most bacteria and fungi found in the root canal area such as *S. aureus, E. coli,* and *P. aeruginosa*. The efficacy of iodine is increased in an acid environment, which is commonly found at sites of inflammation characteristic in infected root canals. Therefore, as the gutta percha cone breaks down due to tissue secretions, the iodine component will become effective.

The form of iodine to be used in the present invention is triiodomethane, also known as iodoform. This form dissipates only slightly, and is inert except when it comes into contact with tissue secretions. The iodoform will then gradually release its free iodine. A 5–10% concentration of iodoform has been shown to be necessary as some effectiveness will be lost due to the leaching out process.

The iodoform is an excellent biocide and antiseptic within the root canal based upon the formation ZnI and free iodine within and the along the wall of the gutta percha cone. The deposit of iodine acts as an inhibitory and cidal agent on any bacteria, either in the inadequately sealed canal itself or brought to the site by the inflammatory response. Iodoform has been shown to be non-irritating when absorbed into tissue through the root canal. The iodoform component of the gutta percha cone only will be active when the cone is failing under the conditions of tissue leakage of poor adaptation. Otherwise the iodine will remain inert in the gutta percha cone.

This new formulation of the gutta percha cone will work as a selective antimicrobial to help insure root canal success only where there is failure of the cone due to poor mechanical preparation, poor adaptation of the cone leading to incomplete obduration of the root canal, or failure to remove all bacteria from the infected root canal.

The antimicrobial gutta percha cone will therefore act as further protection against infection, irritation, and failure of the root canal filling agent.

It is understood that the above description is illustrative only, small variations in the concentration of the formula components could be made without departing from the intended scope of the claim.

What is claimed is:

1. A gutta percha cone, comprising:

20% gutta percha;

55–60% zinc oxide;

10% radiopaque agent consisting of barium sulphate;

5–10% antimicrobial agent consisting of triiodomethane;

5% wax or resin.

* * * * *